United States Patent [19]
Vonier et al.

[11] Patent Number: 5,499,898
[45] Date of Patent: Mar. 19, 1996

[54] APPARATUS FOR TESTING CONDOMS

[75] Inventors: Nathan Vonier, Hermitage, Tenn.; Jim Whitten, Albany, Ga.

[73] Assignee: Agri Dynamics, Inc., Albany, Ga.

[21] Appl. No.: 334,744

[22] Filed: Nov. 4, 1994

[51] Int. Cl.$^6$ .......................... B65G 49/05; B65G 51/02
[52] U.S. Cl. .......................... 414/755; 29/235; 406/155; 414/598; 414/609; 414/648
[58] Field of Search ................... 29/235; 406/87, 406/191, 192, 155; 209/905, 906; 414/598, 609, 648, 755

[56] References Cited

U.S. PATENT DOCUMENTS

Re. 30,410  10/1980  Povlacs .................... 414/755 X
3,992,766  11/1976  Field ............................ 29/235
5,014,407   5/1991  Boughten et al. ............ 29/235

Primary Examiner—Michael S. Huppert
Assistant Examiner—Janice L. Krizek
Attorney, Agent, or Firm—Thomas C. Saitta

[57] ABSTRACT

The invention disclosed is an apparatus for automatically testing condoms comprising a retrieving mechanism to present condoms from a large batch receptacle to an orienting mechanism, the orienting mechanism to orient each condom into the same configuration and orientation, a suction mechanism to move the condoms through the apparatus, a receiving mechanism to receive the oriented condom and position each condom onto a loading mechanism, the loading mechanism for loading the condom onto the testing mandrel, a mandrel shuttling mechanism to move the mandrels to the test position and a condom testing mechanism.

11 Claims, 4 Drawing Sheets

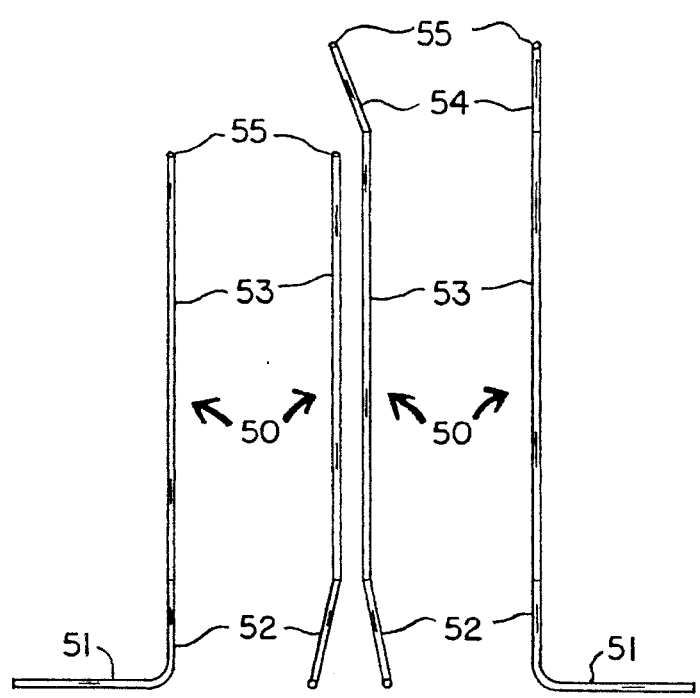
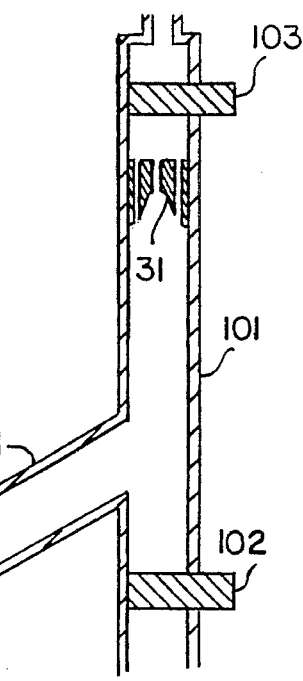
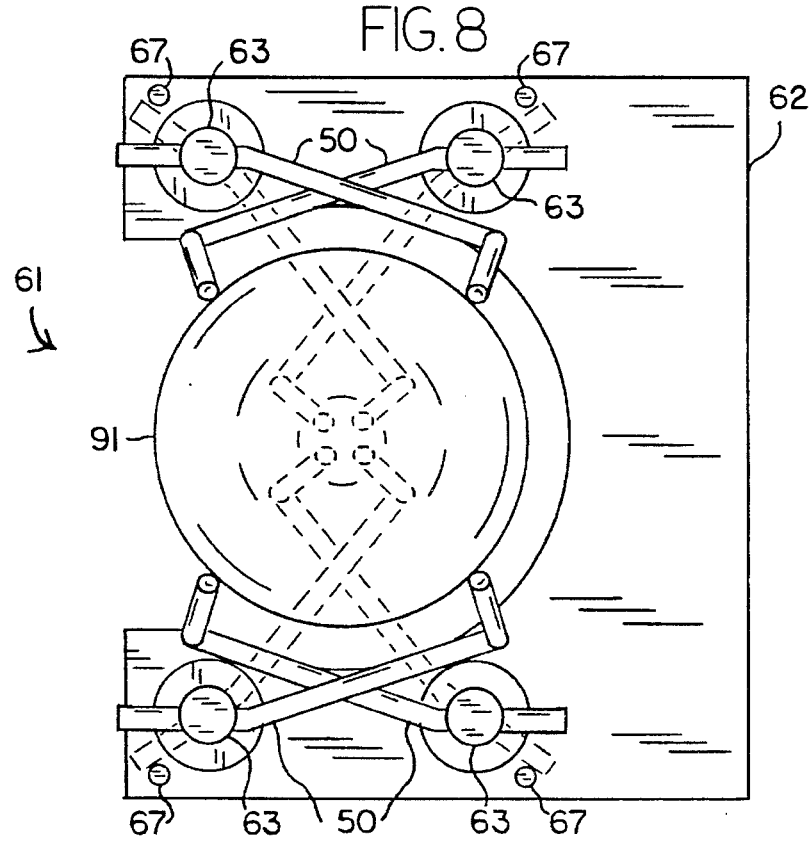

5,499,898

APPARATUS FOR TESTING CONDOMS

BACKGROUND OF THE INVENTION

This invention relates generally to the field of apparatus for testing condoms, and more particularly to the field of condom testing apparatus which automatically handle, orient and load condoms onto mandrels for testing.

It is necessary in the manufacture of condoms to test each individual condom for minute apertures or holes prior to packaging and sale. Testing devices are well known which utilize a metal mandrel onto which the condom is loaded, the mandrel then being passed across an electrically charged net. If current passes between the net and the mandrel, the condom is defective and is rejected. Because of the composition and lack of structure of condoms, it is the current state of the art to hand load each condom onto the mandrel, automatic devices not being capable of handling, orienting and loading the condoms. This is a very slow and labor intensive process.

It is an object of this invention to provide for a condom testing apparatus in which the condoms are automatically, reliably and rapidly retrieved from a general non-oriented, randomly dispersed batch, successively oriented into a particular configuration and orientation, and then loaded onto the mandrels for testing in the conventional manner.

SUMMARY OF THE INVENTION

The invention comprises in general retrieving means to present condoms from a large batch receptacle to orienting means, orienting means to orient each condom into the same configuration and orientation, suction means to move the condoms through the apparatus, receiving means to receive the oriented condom and position each condom onto loading means, loading means for loading the condom onto the testing mandrel, mandrel shuttling means to move the mandrels to the test position and condom testing means.

The suction means can comprise any type of device capable of creating a pressure differential such that air and objects are drawn through the orienting means and into the receiving means. The receiving means may comprise an apertured receptacle or nozzle, where the suction means draws air through the apertures to pull the condom through the orienting means and into the receiving means, from which the condom may be transferred onto the loading means. The orienting means comprises a long circular tube, the inner diameter of the tube being sized slightly smaller than the outer diameter of the ring on the condom, such that contact between the ring and the inner wall of the orienting tube slows the ring as it is pulled through the tube. Because the ring of the condom acts as an anchor, the nipple or tip end of the condom will be drawn forward by the suction means, thereby orienting each condom into the same configuration.

The retrieving means is a mechanical device which is capable of delivering individual condoms to the orienting tube, and may comprise an individual retrieval tube which is reciprocated into a large receptacle containing a number of non-oriented condoms. A suction is drawn through a small opening in the retrieval tube, enabling the retrieval tube to retrieve one condom only. As the retrieval tube reciprocates, the condom is positioned adjacent the orienting tube, where the suction means pulls the condom from the retrieval tube and into the orienting tube for delivery to the receiving means. In practice, a number of orienting tubes, with a corresponding number of loading means and receiving means, will be incorporate into a single condom testing or manipulating apparatus.

The receiving means is positioned in line between the orientation means and the loading means. The suction means draws each condom from the orienting means and positions it such that either the open end of the condom allows access to expansion rods of the loading means or, preferably, such that the condom can be dropped onto the expansion rods of the loading means.

The loading means is mounted onto a track, the loading means comprising a number of expansion rods which occupy a relatively restricted area in the rest position in order to receive a condom, but which can be expanded around the mandrel to stretch the condom onto the mandrel. The configuration of the carriage and mount holding the expansion rods allows the carriage to be passed over the length of the mandrel into a recessed position to allow subsequent movement of the loaded mandrel for testing purposes. The carriage is mounted onto a track such that it receives the condom from a condom retaining means at the uppermost portion of the track and is brought downward on a line such that the central axis of the group of expansion rods is on the same line as the central axis of a mandrel in the loading position. The mandrel expands the expansion rods, thereby stretching the condom. The movement of the carriage down and past the mandrel strips the condom onto the mandrel, and the mandrel can now be moved for testing and the carriage returned to the upper position. This cycle is then repeated for successive condoms.

The condom testing means, mandrel shuttling means and condom removal means are known in the industry and these individual components are incorporated into the apparatus in a suitable manner in order to accomplish the overall task.

BRIEF DESCRIPTION OF THE DRAWINGS

FIG. 7 is a combination of front and side views of the two types of expansion rod configurations.

FIG. 8 is a view illustrating the initial receiving positioning of the expansion rods and the mandrel loading positioning.

FIG. 12 is a view of the preferred embodiment for the receiving means, where a Y-shaped chamber is used so that the condom can be dropped onto the expansion rods.

DETAILED DESCRIPTION OF THE INVENTION

Figure 1:
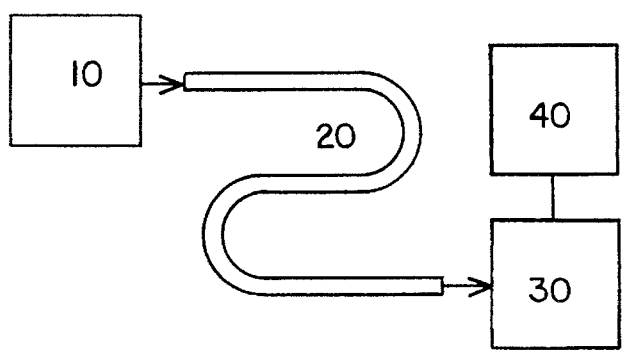
FIG. 1 is a stylized schematic showing the general components of the apparatus.

With reference now to the drawings, the invention will be described in terms of the best mode and preferred embodiment. The invention is an apparatus for testing condoms comprising means to retrieve condoms, means to orient the condoms and deliver them to a receiving means, from which the condoms are placed onto loading means and loaded onto testing mandrels, which are then shuttled to testing means to test for defective condoms. Condoms 90 are thin-walled, tubular objects made of latex or similar elastic material and comprise a nipple or tip end 71, a body 72 and a ring 73 formed by rolling up the condom at the open end 74. As shown in FIG. 1, the retrieving and orienting part of the invention comprises generally retrieving means 10, orientation means 20, receiving means 30 and suction means 40. Retrieving means 10 comprises a mechanism to present or insert a single condom 90 into orientation means 20. Suction means 40 is any suitable device known in the art capable of producing sufficient pressure differential to draw air and condoms 90 through orientation means 20. For example, suction means 40 may comprise a blower or vacuum pump appropriately connected by conduits or a manifold device to create a suction draw in one or more orientation means 20.

Orientation means 20 in the preferred embodiment comprises a long tube 21 having an inner wall 22 with inner diameter 23. The tube 21 is impermeable to air and can be flexible or rigid. It is preferred that tube 21 have a number of curved or coiled portions rather than being strictly linear. The inner wall 22 is preferably smooth. Tube 21 has an inlet opening 24 for receiving the non-oriented condoms and an outlet opening 25 for dispensing the condoms 90 to the receiving means 30. Air is drawn into inlet 24 and out of outlet 24 by suction means 40. The exact inner diameter 23 of tube 21 is a function of the size of the ring 73 of the particular condoms 90 being oriented, and for typical condoms 90 is preferably sized between one and one and a half inches, with the preferred inner diameter 23 being approximately one and one quarter inches. It is preferable that tube 21 be relatively long to insure that the condoms 90 have sufficient time and distance to properly orient, and a total length between 35 and 100 feet is suitable, with a length of approximately 75 feet being preferred.

Figure 6:
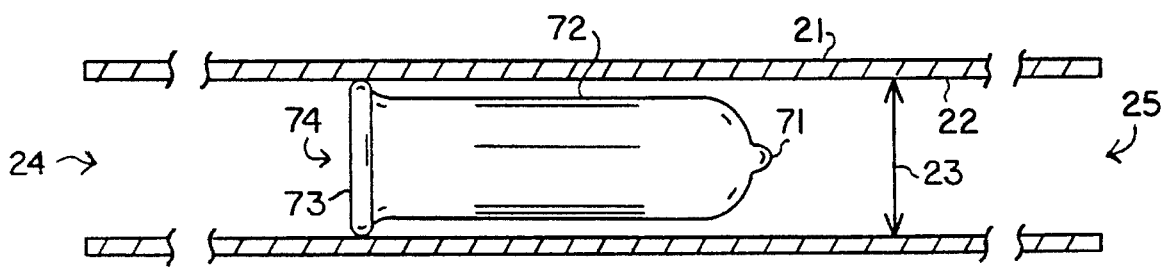
FIG. 6 is a cross-sectional view of a condom as oriented inside the orienting tube.

Orientation means 20 accomplishes the task of orienting a non-oriented, non-configured condom 90 introduced into inlet opening 24 because the inner diameter 23 of inner wall 22 is sized to be slightly smaller than the outer diameter of condom ring 73. When inserted in inlet opening 24, the condom 90 may be folded, twisted and positioned in any random orientation and configuration. As seen in FIG. 6, as the condom 90 is drawn towards outlet opening 25 by suction means 40, the inner wall 22 compresses flexible ring 73. The friction between the ring 73 and the inner wall 22 creates a drag on the ring 73 but does not affect the main body 72 and tip 71 of the condom 90. The friction is not so great as to stop progress of the condom 90 through tube 21, it only acts to slow it down. No matter the entry orientation and configuration of the condom 90, over the length of the orienting tube 21 the drag on the ring 73 results in the tip 71 being pulled to the front, i.e., in the direction of travel, by suction means 40. The curved or coiled portions of tube 21 increase the orientation efficiency, possibly because the different radial distances of the walls within each curved portion enable greater alignment of twisted sections of the condom 90. Every condom 90 thus exits outlet opening 25 with the tip 71 in front, followed by the untwisted main body 72 and then ring 73.

Figure 4:
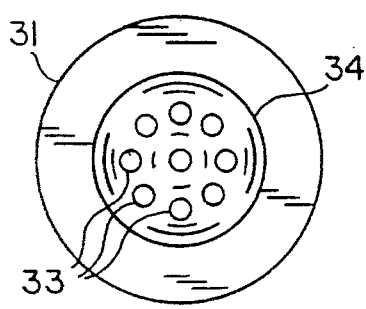
FIG. 4 is an end view of the nozzle receptacle.
Figure 5:
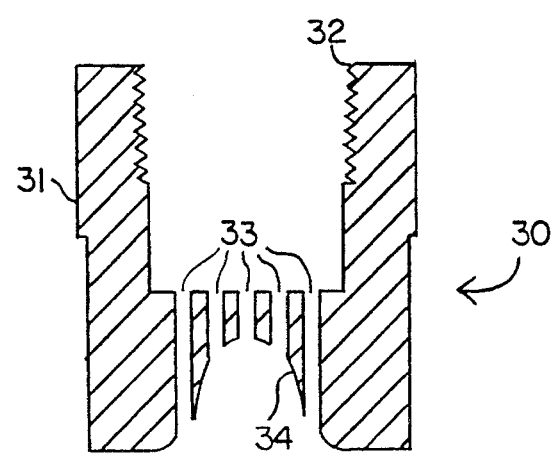
FIG. 5 is a cross-sectional view of the nozzle receptacle.

The apparatus is adapted to present each condom 90 in the same orientation and configuration to the receiving means 30, which can be any device adapted to retain the condom 90 in the correct position. In the embodiment shown in FIGS. 4 and 5, the receiving means 30 comprises receptacle nozzle 31, which is connected to conduit means of suction means 40 via threaded fitting 32. Nozzle 31 has a number of apertures 33 positioned generally symmetrically within a cup shaped wall 34, and suction means 40 draws air through these apertures 33. As the condom 909 exits outlet opening 25 of orienting tube 21, the tip 71 is drawn to apertures 33 and into the cup portion 34 of nozzle 31, where it is held in place until the suction is released. Nozzle 31 can then be removed from orientation tube 21 to deposit the condom 90 where required for further manipulation or testing, or tube 21 can be moved from nozzle 31, or a gated multiple outlet housing can be used such that movement of neither tube 21 or nozzle 31 is necessary to deliver the condom 90. Preferably nozzle 31 is vertically oriented such that the condom 90 hangs downward with the tip 71 at the top and the open end 74 on the bottom.

Figure 2:
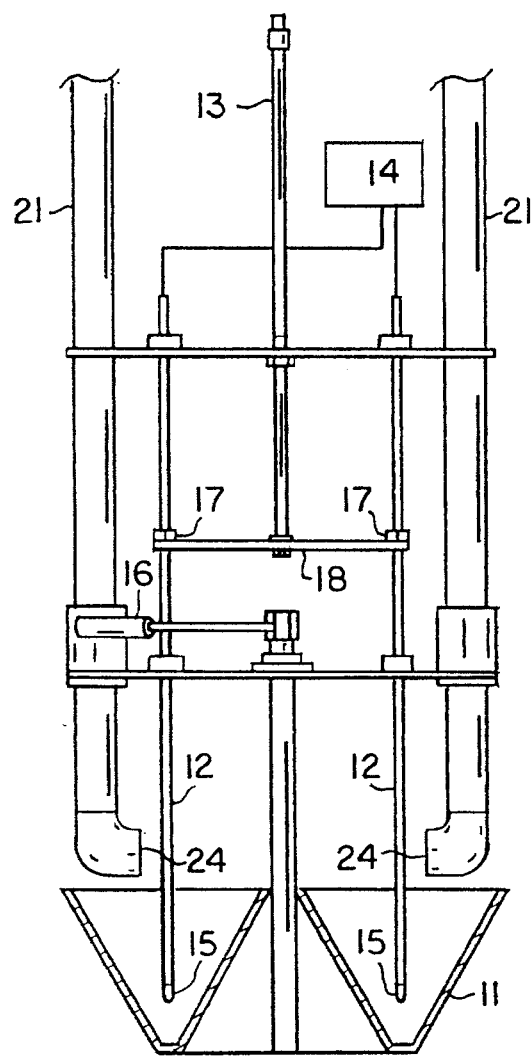
FIG. 2 is a view of the loading means and orienting means, with the loading means shown in the capture position.
Figure 3:
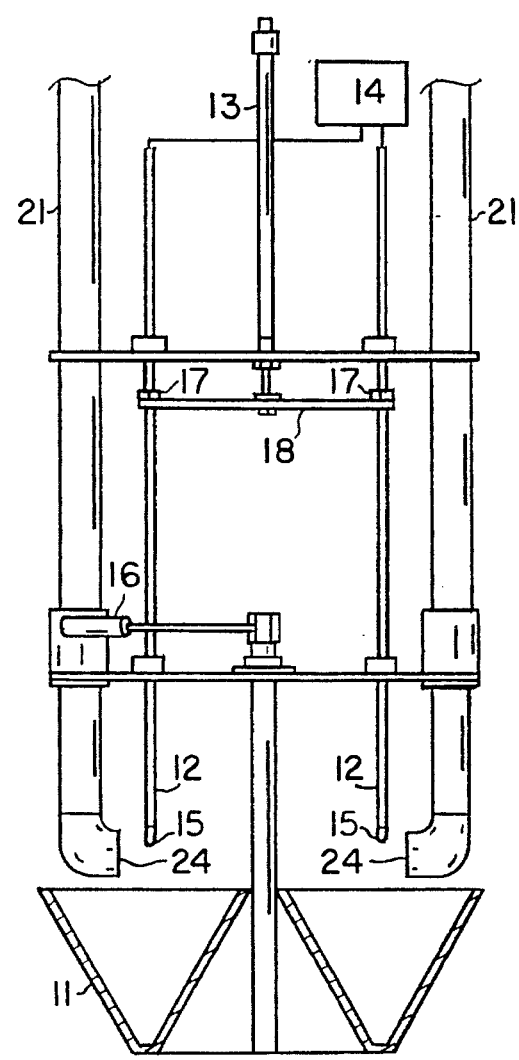
FIG. 3 is a view of the loading means and orienting means, with the loading means shown in the presentation position.

Because the apparatus is designed to greatly increase the speed with which condoms 90 can be oriented and positioned, it is preferable that retrieving means 10 comprise a mechanical system for successively retrieving individual condoms 90 from a receptacle containing a large number of non-oriented, randomly configured condoms 90 and delivering each individual condom 90 to the orientation means 20. A preferred embodiment for retrieving means 10 adapted for use with plural orientation means 20 is shown in FIGS. 2 and 3. Condom receptacle 11 is constructed to receive and hold a large number of condoms 90. It is preferred that the receptacle 11 be configured such that as condoms 90 are removed by the retrieval tubes 12, more condoms 90 will be positioned at the correct location for retrieval during the next cycle. An inverted cone shape preferably vibrated by receptacle movement means 16 will accomplish this, or in the preferred embodiment as shown a circular trough having a dual cone-shaped cross-section which is rotated by receptacle movement means 16 adequately positions condoms 90 for successive retrieval by the reciprocating retrieval tubes 12. The vibration or rotation of receptacle 11 compensates for the packing action of the retrieval tubes 12 as they reciprocate vertically. Retrieval tubes comprise small tubes having an apertured tip 15, through which is drawn a small suction by retrieval suction means 14, shown here schematically. Retrieval suction means 14 can be any suitable device known for creating a pressure differential sufficient to retain a condom 90 against the apertured tip 15 as it is drawn upward.

The operation of retrieving means 10 is illustrated by comparison of FIG. 2 with FIG. 3. FIG. 2 illustrates the capture or selection position. The retrieval tubes 12 are dropped into the receptacle 11 by reciprocating means 13, which can comprise an air cylinder or any other suitable mechanical configuration for vertically moving the retrieval tubes 12. The retrieval tubes 12 are preferably not fixed to reciprocating means 13, but instead have free travel in the upward direction. This is accomplished by the provision of a collar 17 attached to the retrieval tube 12. As the reciprocating means 13 is lowered and the apertured tip 15 contacts the top of the condom pile, the retrieval tube 12 remains stationary while the lower plate 18 moves to its extreme downward position. As the lower plate 18 is brought upward by reciprocating means 13, it contacts collar 17 and raises the apertured tip 15 and captured condom 90 to the proper height adjacent the inlet opening 24 of the orienting tube 21, as shown in FIG. 3. The greater suction from suction means 40 strips the condom 90 from the apertured tip 15 of retrieval tube 12, pulling it through the orienting tube 21 as previously described. The empty retrieval tube 12 is then lowered into the receptacle 11 to retrieve another condom 90, and this cycle is repeated.

The loading means is an apparatus for loading condoms 90 onto a mandrel 91 which is shaped in matching configuration to the condom 90 and comprises a movable carriage assembly 60 upon which are mounted a number of expansion rods 50 for receiving and stretching a condom 90, whereby the condom 90 is deposited onto the mandrel 91 by movement of the carriage 60. The expansion rods 50 act as runners on the surface of the mandrel 91, such that there is no resistance or contact between the mandrel 91 and the condom 60 until the tip of the condom 90 is brought down onto the tip of the mandrel 91.

Figure 9:
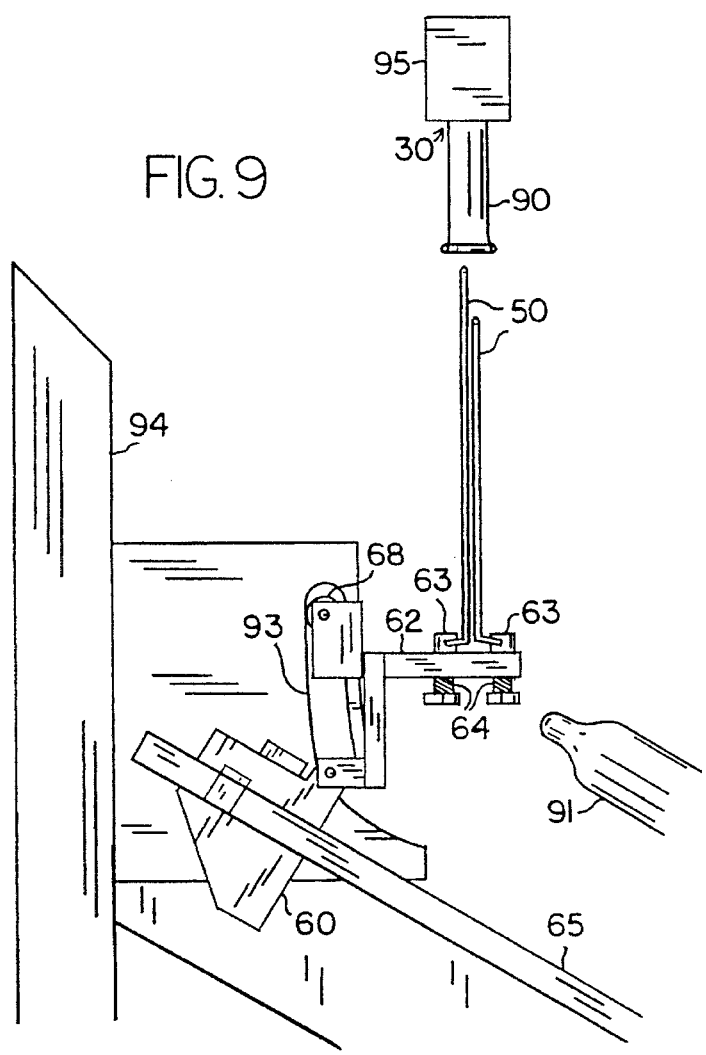
FIG. 9 is a view of the rod carriage in the receiving position.

The carriage assembly 60 and expansion rods 50 can be seen in FIG. 9. This illustration shows the rods 50 in the receiving position to receive the condom 90 prior to loading it onto the mandrel 91. The carriage assembly 60 is comprised of a rod mount 62 to which are attached the multiple expansion rods 50. The carriage assembly 60 is mounted onto a linear carriage track 65 which allows reciprocal movement of the carriage 60 past the mandrel 91 to be loaded. Condom retaining means 95 holds the condom 90 in a vertical position with the tip of the condom 90 on top so that the base, ring and open end of the condom 90 hang downward. Condom receiving means 30 can be any suitable mechanism for presenting the condom 90 in the described manner, and can comprise mechanical or suction means to hold the tip for release and to keep the body expanded to allow for insertion of the expansion rods 50 into the condom 90. Alternatively and preferably, it has been found that simply maintaining the tip of the condom 90 at the uppermost position and then releasing it to fall onto the expansion rods 50 is the simplest and most efficient way to place the condom 90 onto the expansion rods 50. As the condom 90 falls, air fills the interior through the open end, thus expanding the condom 90 like a parachute to settle onto the rods 50.

Figure 11:
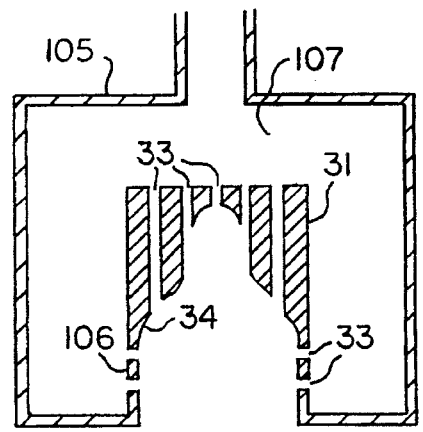
FIG. 11 is a view of one embodiment of the receiving means where suction is used to expand the condom to allow insertion of the expansion rods.

In one embodiment, as shown in FIG. 11, the receiving means 30 comprises the nozzle 31 mounted into an expansion housing 105 which has an internal chamber 107, with both the nozzle 31 and the internal chamber connected to the suction means 40. The internal chamber 107 is bounded by perforated internal wall 106. When the condom 90 is drawn from the orienting tube 21, the tip 71 of the condom 90 is sucked into the cup 34 of the nozzle 31. Suction is then drawn through the perforated internal wall 106 to expand the body 72 of the condom 90 outward. The expansion housing 105 is then reciprocated from the orienting tube 21 and the expansion rods 50 are inserted into the condom 90. The suction is then stopped or reversed, placing the condom 90 onto the rods for transfer to the mandrel 91.

Because the above embodiment requires movement of several components, the preferred embodiment, as shown in FIG. 12, utilizes a multiple outlet housing 101 having a generally Y-shaped or branched configuration. The condom 90 is drawn from the orienting tube 21 and the tip 71 sucked to the cup 34 of the nozzle 31. The orienting tube 21 is connected to the side of the housing 101 at an angle. The suction is then turned off, or preferably a suction control gate or valve 103 seals off the suction means 40 at the same time as a loading gate 102 is opened at the bottom of the housing 101. The housing 101 is positioned directly over the expansion rods 50, as shown in FIG. 9, and the condom 90 falls onto the rods 50. Since the orienting tube 21 is to the side, the condom 90 falls past this outlet and directly out the bottom of the housing 101.

Expansion rods 50 are preferably thin, elongated members of small cross-sectional diameter composed of a rigid metal or like material. While rods 50 may be configured in many various shapes, the configuration shown in FIGS. 7 and 8 has been found to be very effective in loading the condom 90 onto the mandrel 91. It is best to use at least three, and preferably four or more rods 50 to expand the condom 90 as it is drawn over the mandrel 91. The object is to minimize and preferably completely eliminate any contact between the sides of the mandrel 91 and the sides of the condom 90. The use of four rods 50 positioned 90 degrees apart in the expanded configuration is preferred. The rods 50 are pivotally mounted onto a generally U-shaped mount 62 surrounding a mandrel receiving opening 61. The connecting segment 51 of each rod 50 is attached to a pivoting post 63, which is biased by a spring 64 such that the rods 50 occupy a rest position, shown by the dotted lines in FIG. 8, with the tips 55 of all the rods 50 being relatively contiguous or adjacent to one another and the main body segments 53 being generally parallel and also contiguous or adjacent each other. A positioning pin 67 is used to maintain the rods 50 in this position. It is necessary that the tips 55 occupy a relatively small area so that they will not interfere with the drop of the condom 90, as the tip of the condom 90 should end up resting on the tips 55 of the rods 50. In the preferred configuration, as seen in FIG. 7, each rod 50 is comprised of a connecting segment 51 for insertion into the pivoting posts 63, a main body segment 53, a transition segment 52 joining the main body 53 and the connecting segment 51 angled such that the central axis of the main body segment 53 does not intersect the central axis of the connecting segment 51, and a blunt or rounded tip 55. Preferably, one rod 50 is slightly longer than the others and is provided with a centering extension segment 54, whereby the tip 55 of this rod 50 is positioned on the central axis of the grouping of all the rods 50. This results in only a single uppermost tip 55, thus insuring that the condom 90 will not be snagged as it is dropped onto the rods 50. This configuration is preferred as it enables the main body segment 53 of each rod 50 to remain parallel to the sides of the mandrel 91 as they are passed down over it.

Figure 10:
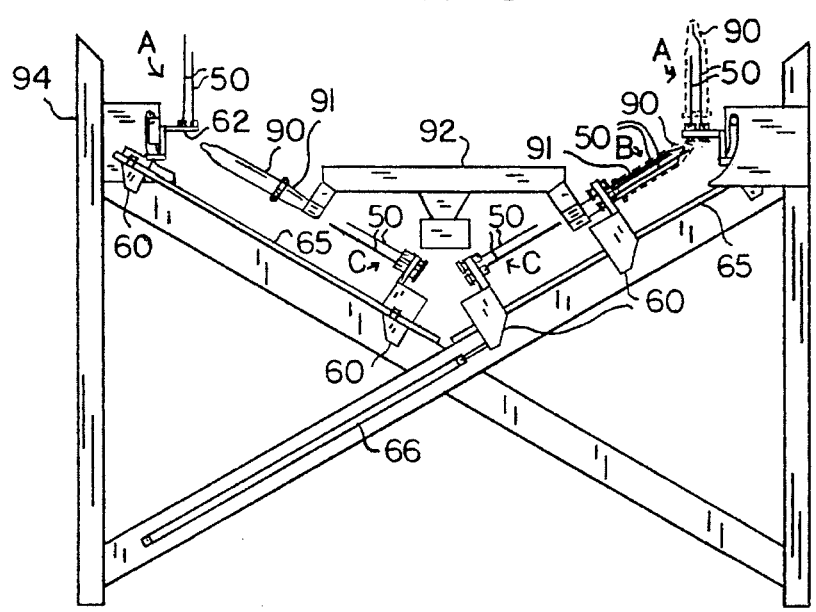
FIG. 10 is a view of the loading apparatus showing rod carriages in various positions of the loading cycle.

FIG. 10 shows an apparatus with two carriage tracks 65. A reciprocating means 66, such as an air cylinder, mounted onto a frame 94 moves each carriage 60 up and down track 65. Three positions A, B and C are illustrated. Position A is the receiving position previously described at which the condom 90 is placed onto the expansion rods 50. Position B is the mandrel loading position, and position C is the retracted position. After the condom 90 is placed onto the rods 50, the carriage is moved down along track 65 to mandrel 91. The mandrel receiving opening 61 is positioned opposite from the connecting means attaching the carriage 60 to the track 65, in the upward orientation as shown. The mandrel 91 is mounted so as to depend from a mandrel shuttle 92, with the connecting means being on top of the mandrel 91. As the carriage assembly 60 is brought down to mandrel 91, it freely passes the mandrel 91 because of the mandrel receiving opening 61. As the tip of the mandrel 91 encounters the transition segments 52 of the rods 50, they are forced outward to the positions shown by the solid lines in FIG. 8. This stretches the condom 90 to a size greater than the outer circumference of the mandrel 91, the main body segments 53 of the rods 50 acting as runners and spacers along the length of the mandrel 91. As the carriage 60 is brought lower, the tip of the mandrel 91 encounters the tip of the condom 90 and acts as an anchor, as shown in position B of FIG. 4. The carriage 60 continues downward and the expansion rods 50 are pulled out of the condom 90, leaving the condom 90 fully loaded onto the mandrel 91. With the carriage 60 now in the fully retracted position C, the mandrel shuttle 92 can move the loaded mandrel 91 to the testing and then the condom removal position. When mandrel 91 is moved away from track 65, the carriage 60 is returned to the receiving position A for another cycle.

As explained, it is preferable that the rods 50 be in a vertical position to receive the condom 90, especially when the gravity drop method is utilized. For removal of the condom 90 from the mandrel 91 after testing, however, it is preferred that the mandrel 91 be non-vertically oriented. As shown in FIG. 10, this requires that the expansion rods 50 be repositioned from the vertical alignment of position A to the alignment of position B which matches the mandrel 91 alignment. In this embodiment, this realignment is accomplished by pivotally attaching the rod mount 62 to carriage 60 and positioning a roller 68 which enters an orienting slot 93 on frame 94 at the upper end of track 65. As carriage assembly 60 is moved upward by reciprocating means 66, the roller 68 pivots the mount 62 such that the rods 50 are vertically aligned. As the carriage 60 is lowered, the mount 62 pivots back into its resting position and the rods 50 are aligned with mandrel 91.

It is understood that those skilled in the art may become aware of equivalents or substitutions for the elements set forth above. The full scope and definition of the invention therefore is to be set forth in the following claims.

We claim:

1. An apparatus for testing condoms comprising:
   (A) retrieving means to deliver condoms to orienting means;
   (B) orienting means to orient said condoms into a particular configuration and orientation;
   (C) suction means to draw said condoms through said orienting means and into a receiving means;
   (D) said receiving means for placing said condoms onto a loading means;
   (E) said loading means for loading said condoms onto a mandrel.

2. The apparatus of claim 1, where said orienting means comprises a long orienting tube having an inlet opening for receiving condoms and an outlet opening for delivering said condoms oriented with the tip first and followed by the ring and open end to said receiving means.

3. The apparatus of claim 1, where said loading means comprises a carriage assembly comprising a number of expansion rods attached to a mount, said expansion rods each comprising a main body segment and tip, whereby said main body segments and said tips of said rods are positioned adjacent each other in a rest position to receive a condom, but may be expanded outward by a mandrel such that said rods expand said condom to a size greater than said mandrel, said carriage assembly being adapted to pass over said mandrel such that said mandrel removes said condom from said rods.

4. The apparatus of claim 1, where said retrieving means comprises one or more retrieval tubes, a receptacle to contain said condoms, reciprocating means to reciprocate said retrieval tubes into and out of said receptacle, and retrieval suction means connected to said retrieval tubes to hold said condoms, whereby said reciprocating means positions said condoms held by said retrieval tubes adjacent to said orienting means such that said suction means removes said condoms from said retrieval tubes.

5. The apparatus of claim 1, where said receiving means comprises a branched multiple outlet housing comprising a nozzle mounted at one outlet to receive said condom from said orienting means, where said orienting means enters said housing through another outlet at the side of said housing, gate means to seal said suction means, and gate means to open a bottom outlet to release said condom onto said loading means when said suction means is sealed.

6. The apparatus of claim 2, where said loading means comprises a carriage assembly comprising a number of expansion rods attached to a mount, said expansion rods each comprising main body segment and tip, whereby said main body segments and said tips of said rods are positioned adjacent each other in a rest position to receive a condom, but may be expanded outward by a mandrel such that said rods expand said condom to a size greater than said mandrel, said carriage assembly being adapted to pass over said mandrel such that said mandrel removes said condom from said rods.

7. The apparatus of claim 2, where said retrieving means comprises one or more retrieval tubes, a receptacle to contain said condoms, reciprocating means to reciprocate said retrieval tubes into and out of said receptacle, and retrieval suction means connected to said retrieval tubes to hold said condoms, whereby said reciprocating means positions said condoms held by said retrieval tubes adjacent to said inlet opening of said orienting tube such that said suction means removes said condoms from said retrieval tubes.

8. The apparatus of claim 2, where said receiving means comprises a branched multiple outlet housing comprising a nozzle mounted at one outlet to receive said condom from said orienting means, where said orienting means enters said housing through another outlet at the side of said housing, gate means to seal said suction means, and gate means to open a bottom outlet to release said condom onto said loading means when said suction means is sealed.

9. The apparatus of claim 6, where said retrieving means comprises one or more retrieval tubes, a receptacle to contain said condoms, reciprocating means to reciprocate said retrieval tubes into and out of said receptacle, and retrieval suction means connected to said retrieval means to hold said condoms, whereby said reciprocating means positions said condoms held by said retrieval means adjacent to said inlet opening of said orienting tube such that said suction means removes said condoms from said retrieval means.

10. The apparatus of claim 6, where said receiving means comprises a branched multiple outlet housing comprising a nozzle mounted at one outlet to receive said condom from said orienting means, where said orienting means enters said housing through another outlet at the side of said housing, gate means to seal said suction means, and gate means to open a bottom outlet to release said condom onto said loading means when said suction means is sealed.

11. The apparatus of claim 9, where said receiving means comprises a branched multiple outlet housing comprising a nozzle mounted at one outlet to receive said condom from said orienting means, where said orienting means enters said housing through another outlet in the side of said housing, gate means to seal said suction means, and gate means to open a bottom outlet to release said condom onto said loading means when said suction means is sealed.

* * * * *